(12) United States Patent
Kim et al.

(10) Patent No.: US 10,912,856 B2
(45) Date of Patent: Feb. 9, 2021

(54) BACTERIAL ADSORPTION DRESSING WITH NONPHOTOCATALYST AND METHOD OF MANUFACTURING THE SAME

(71) Applicant: SAMBO ADVANCED MATERIALS INC., Daegu (KR)

(72) Inventors: Hyung Joon Kim, Daegu (KR); Jeon Young Kang, Daegu (KR); Jeong Ha Lee, Daegu (KR)

(73) Assignee: SAMBO ADVANCED MATERIALS INC., Daegu (KR)

( * ) Notice: Subject to any disclaimer, the term of this patent is extended or adjusted under 35 U.S.C. 154(b) by 0 days.

(21) Appl. No.: 15/717,426

(22) Filed: Sep. 27, 2017

(65) Prior Publication Data

US 2018/0193514 A1 Jul. 12, 2018

(30) Foreign Application Priority Data

Jan. 10, 2017 (KR) ........................ 10-2017-0003363

(51) Int. Cl.

| | | |
|---|---|---|
| *A61L 15/18* | (2006.01) | |
| *A61L 15/26* | (2006.01) | |
| *A61L 15/22* | (2006.01) | |
| *A61L 15/42* | (2006.01) | |
| *A61L 15/44* | (2006.01) | |
| *A61F 13/00* | (2006.01) | |
| *D04B 1/22* | (2006.01) | |
| *A61L 15/46* | (2006.01) | |
| *D04B 21/16* | (2006.01) | |

(52) U.S. Cl.
CPC ........ *A61L 15/18* (2013.01); *A61F 13/00063* (2013.01); *A61L 15/225* (2013.01); *A61L 15/26* (2013.01); *A61L 15/425* (2013.01); *A61L 15/44* (2013.01); *A61L 15/46* (2013.01); *D04B 1/22* (2013.01); *D04B 21/16* (2013.01); *A61L 2300/102* (2013.01); *A61L 2300/112* (2013.01); *A61L 2300/404* (2013.01); *A61L 2300/406* (2013.01); *A61L 2300/606* (2013.01); *A61L 2400/12* (2013.01)

(58) Field of Classification Search
CPC ........ A61L 15/18; A61L 15/46; A61L 15/425; A61L 15/26; A61L 15/44; A61L 15/225; A61L 2400/12; A61L 2300/404; A61L 2300/102; A61L 2300/112; A61L 2300/606; A61L 2300/406; D04B 21/16; D04B 1/22; A61F 13/00063; A61F 13/00017; A61F 13/00029
See application file for complete search history.

(56) References Cited

U.S. PATENT DOCUMENTS

| | | |
|---|---|---|
| 2006/0057343 A1 | 3/2006 | Tsuji et al. |
| 2009/0216168 A1* | 8/2009 | Eckstein ........... A61F 13/00063 602/43 |

FOREIGN PATENT DOCUMENTS

| | | | |
|---|---|---|---|
| JP | 2001248066 A | * | 9/2001 |
| JP | 2001248066 A | | 9/2001 |
| JP | 2002308712 A | | 10/2002 |
| JP | 2009233239 A | * | 10/2009 |
| JP | 6060510 B2 | | 1/2017 |
| KR | 20100021108 A | | 2/2010 |
| KR | 20130065179 A | | 6/2013 |
| KR | 101540061 B1 | | 7/2015 |
| WO | WO-2010052190 A2 | * | 5/2010 ............. A61L 15/18 |

OTHER PUBLICATIONS

Körösi and Dékány, "Preparation and investigation of structural and photocatalytic properties of phosphate modified titanium dioxide", Colloids and Surfaces A: Physiochem Eng Aspects 280: 146-154 (2006) (Year: 2006).*

Yu and Wang, "Photocatalysis and characterization of the gel-derived TiO2 and P-TiO2 transparent thin films", Thin Solid Films 519: 6453-6458 (2011) (Year: 2011).*

Connor and McQuillan, "Phosphate Adsorption onto TiO2 from Aqueous Solutions: An in situ Internal Reflection Infrared Spectroscopic Study", Langmuir 15: 2916-2921 (1999) (Year: 1999).*

Hayashi, JP2009233239, 2009, English Translation from Patent Translate Powered by Google, 4 pages. (Year: 2009).*

Miyauchi, T., JP2001248066, Derwent Abstract, Formation of sterilized gauze from protecting wounded areas such as burns, external injury, involves adhering a metal layer on a base material by sputtering, 2001, Abstract, 4 pages. (Year: 2001).*

* cited by examiner

*Primary Examiner* — Sue X Liu
*Assistant Examiner* — Andriae M Holt
(74) *Attorney, Agent, or Firm* — Heslin Rothenberg Farley & Mesiti P.C.

(57) ABSTRACT

A bacterial adsorption dressing in contact with a wound and a method of manufacturing the bacterial adsorption dressing are provided. A bacterial adsorption dressing with a non-photocatalyst includes a fabric layer including a polyester fiber as a supporter, and a nonphotocatalyst coating layer formed on the fabric layer and including titanium dioxide phosphate.

10 Claims, 5 Drawing Sheets

BACTERIAL ADSORPTION DRESSING WITH NONPHOTOCATALYST AND METHOD OF MANUFACTURING THE SAME

CROSS-REFERENCE TO RELATED APPLICATION

This application claims the benefit of Korean Patent Application No. 10-2017-0003363, filed on Jan. 10, 2017, in the Korean Intellectual Property Office, the disclosure of which is incorporated herein by reference.

BACKGROUND

1. Field of the Invention

One or more example embodiments relate to a wound dressing in contact with a wound and a method of manufacturing the wound dressing, and more particularly, to a bacterial adsorption dressing including a hydrophilic nonphotocatalyst coating layer and a method of manufacturing the bacterial adsorption dressing.

2. Description of the Related Art

Currently, various wound dressings products are required depending on a type of wounds and a necessary environment. Among wound dressing products, an absorption dressing and a cover dressing, such as hydrocolloids, foams, alginates and hydrofibers, are applicable to a deep wound that produces a large amount of fluid, and a filling dressing, such as powder and paste, is applicable to a deep wound or a wound that produces a small amount of fluid.

In the above wound dressing, a main factor may include, for example, a wet environment, an infection, a foreign body, a necrotic tissue, a temperature, an oxygen concentration, a pH, and the like. In addition, ideal dressing requirements include, for example, an ability to maintain an adequate moisture on a surface in contact with a wound, an ability to absorb an exudate, an ease of an attachment to and removal from a wound, an ability to deliver gas and water vapor to the outside, an insulation from the outside, a defensive power against invading bacteria, a defensive power for a human body, a non-toxicity to a human body, an economic feasibility, and other important factors, such as a decrease in a bacterial activity and a degree of a bacterial adsorption.

To this end, research has been conducted on improvement of performance of the above main factors using various ways. However, a degree by which the performance is improved fails to meet market requirements. In particular, research on a wound dressing with a high degree of bacterial adsorption by focusing on a bacterial adsorption is insufficient.

Recently, a method of removing pollutants using photoactivity of a photocatalyst in, for example, an architectural field, is being provided. The photocatalyst is an environment-friendly material to convert photoenergy to chemical energy at a room temperature. Such photocatalysts have been widely applied and practically used in various fields, for example, housing, household appliances, household goods, vehicles, roads, air treatment, water treatment, agriculture, and the like.

The above photocatalysts are attracting attention in recent years due to a bacteria adsorption function in addition to an air purification function, an antifouling function, a water purification function, a deodorization function and a fine dust removal function. The inventors of the present disclosure have paid attention to a nonphotocatalyst that is a kind of photocatalysts and that is capable of performing the above functions even in a light-free environment, in particular, have paid attention to bacterial adsorption properties of the nonphotocatalyst, and have completed the present disclosure by conceiving a technology of manufacturing a dressing of a new concept by applying the nonphotocatalyst to a dressing.

SUMMARY

The present disclosure is to provide a dressing using a nonphotocatalyst including titanium dioxide phosphate that has an excellent bacterial adsorption characteristic. An aspect provides a dressing including a microporous nonphotocatalyst coating layer to effectively maintain a bacterial adsorption characteristic when a nonphotocatalyst functions even in a light-free environment.

According to an aspect, there is provided a bacterial adsorption dressing with a nonphotocatalyst, including a fabric layer including a polyester fiber as a supporter, and a nonphotocatalyst coating layer formed on the fabric layer and including titanium dioxide phosphate.

The bacterial adsorption dressing may further include a support layer including a tencel nonwoven fabric and formed on an opposite side to a side of the fabric layer in contact with the nonphotocatalyst coating layer, and an absorption layer including a rayon nonwoven fabric.

The nonphotocatalyst coating layer may be hydrophilic and may adsorb hydrophobic bacteria by an oxidation reaction.

The titanium dioxide phosphate may have a particle diameter of 6 nanometers (nm) to 15 nm.

The nonphotocatalyst coating layer may have a thickness of 10 micrometers (μm) to 20 μm.

The nonphotocatalyst coating layer may include a microporous surface layer.

The fabric layer may include an inorganic antibacterial material including at least one of zeolite, calcium phosphate, zirconium phosphate and silica gel.

The absorption layer may have a thickness of 500 μm to 2,000 μm and a weight of 60 grams per square meter ($g/m^2$) to 200 $g/m^2$. The support layer may have a thickness of 100 μm to 500 μm and a weight of 20 $g/m^2$ to 60 $g/m^2$. The absorption layer and the support layer may be mechanically bonded to each other.

The absorption layer may further include an airlaid nonwoven fabric.

The bacterial adsorption dressing may further include a pore nonwoven fabric layer formed of a nonwoven fabric including a pore with a size of 2 μm to 10 μm and located between the fabric layer and the absorption layer.

According to another aspect, there is provided a method of manufacturing a bacterial adsorption dressing with a nonphotocatalyst, including preparing a nonphotocatalyst solution, forming a fabric layer including a polyester fabric using a knitting process with a guide bar, and forming a nonphotocatalyst coating layer on the fabric layer using the nonphotocatalyst solution.

The method may further include, after the forming of the nonphotocatalyst coating layer, or between the forming of the fabric layer and the forming of the nonphotocatalyst coating layer, forming a support layer on an opposite side to a side of the fabric layer in contact with the nonphotocatalyst coating layer using a spunlace process, the support layer including a tencel nonwoven fabric, forming an absorption layer including a rayon nonwoven fabric using a needle punching process, and mechanically bonding the absorption layer and the support layer to each other.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
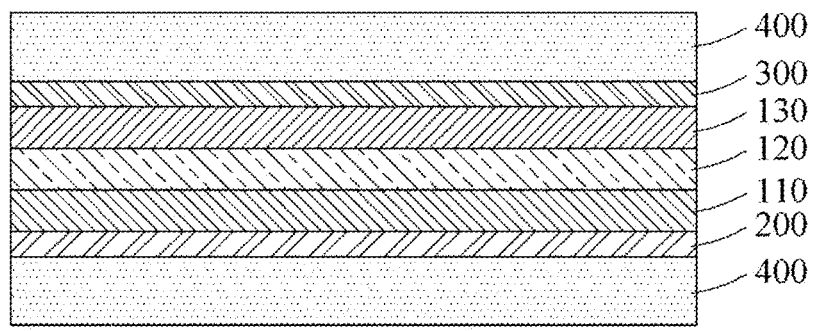
FIG. 1 is a diagram illustrating a configuration of a bacterial adsorption dressing with a nonphotocatalyst according to an example embodiment.

Hereinafter, example embodiments of the present disclosure will be described in detail with reference to the accompanying drawings.

Various modifications may be made to the example embodiments. The example embodiments are not construed as limited to the disclosure and should be understood to include all changes, equivalents, and replacements within the idea and the technical scope of the disclosure.

The terminology used herein is for the purpose of describing particular example embodiments only and is not intended to be limiting of example embodiments. As used herein, the singular forms are intended to include the plural forms as well, unless the context clearly indicates otherwise. It should be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching with contextual meanings in the related art and are not to be construed as an ideal or excessively formal meaning unless otherwise defined herein.

Regarding the reference numerals assigned to components in the drawings, it should be noted that the same components will be designated by the same reference numerals, wherever possible, even though they are shown in different drawings. Also, in describing of example embodiments, detailed description of well-known related structures or functions will be omitted when it is deemed that such description will cause ambiguous interpretation of the present disclosure.

FIG. 1 is a diagram illustrating a configuration of a bacterial adsorption dressing with a nonphotocatalyst according to an example embodiment.

Referring to FIG. 1, the bacterial adsorption dressing includes a fabric layer 110 that includes a polyester fiber as a supporter, and a nonphotocatalyst coating layer 200 that is formed adjacent to the fabric layer 110 and that includes titanium dioxide phosphate.

In an example, the bacterial adsorption dressing may provide a fabric layer in which a supporter is formed of a polyester fiber. Also, the bacterial adsorption dressing may include a hydrophilic coating layer formed on a side of the bacterial adsorption dressing using a nonphotocatalyst including titanium dioxide phosphate.

In this example, the nonphotocatalyst including the titanium dioxide phosphate may have the same mechanism as that of a photocatalyst, however, may generate a hydroxyl radical (.OH) and generate a reactive oxygen by a strong oxidation even though light is absent to effectively adsorb bacteria.

Figure 2:
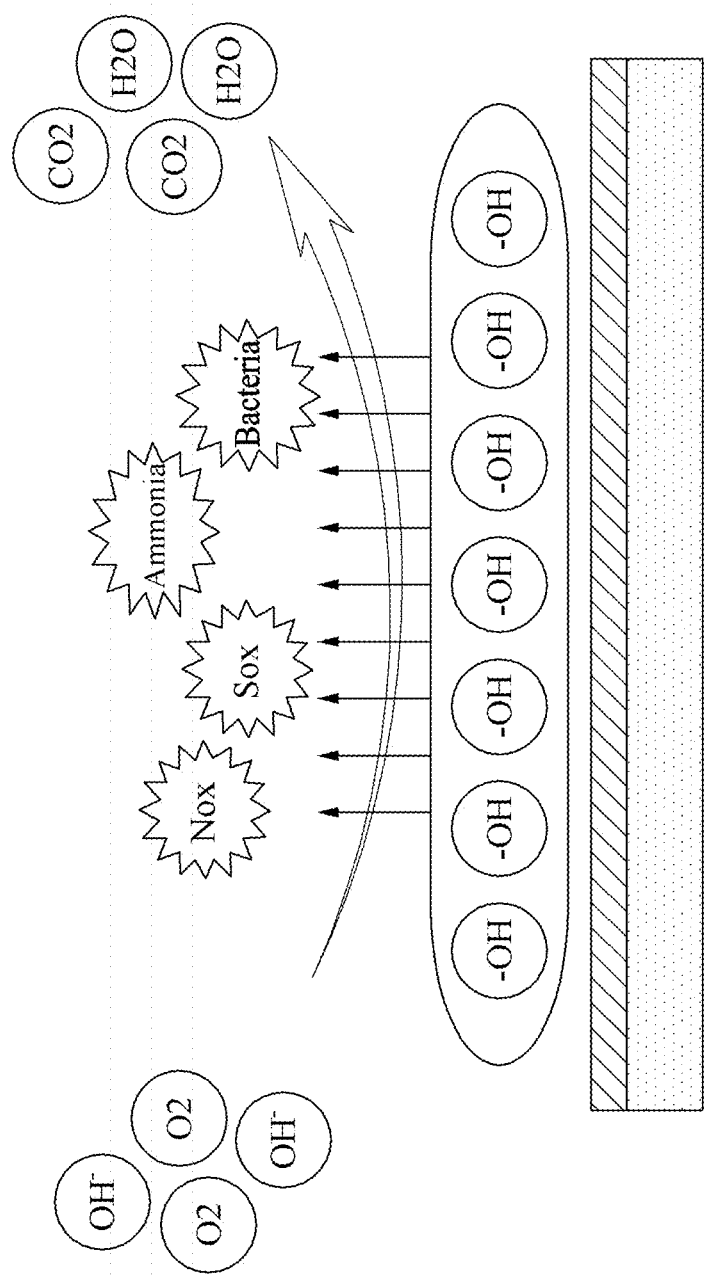
FIG. 2 is a diagram illustrating a process in which a nonphotocatalyst coating layer adsorbs bacteria while generating a reactive oxygen according to an example embodiment.

FIG. 2 is a diagram illustrating a process in which a nonphotocatalyst coating layer adsorbs bacteria while generating a reactive oxygen according to an example embodiment.

Nano-sized titanium dioxide phosphate may be located on a fabric of a fabric layer and may be partially woven into the fabric. Titanium dioxide phosphate particles may react with moisture in the air, to have a bacterial adsorption and antibacterial effect.

Generally, since an organic binder adhesive is used for a photocatalyst in a process of forming a layer, a dryness of the photocatalyst may decrease. Also, since light is not received to the photocatalyst even when the photocatalyst includes a titanium dioxide component, the photocatalyst may not adsorb bacteria. However, a nonphotocatalyst according to an example embodiment may have an excellent adhesiveness even when the organic binder adhesive is not used, and may initiate a reaction by reacting with the air instead of light, to adsorb bacteria even in a dark environment.

Figure 3A:
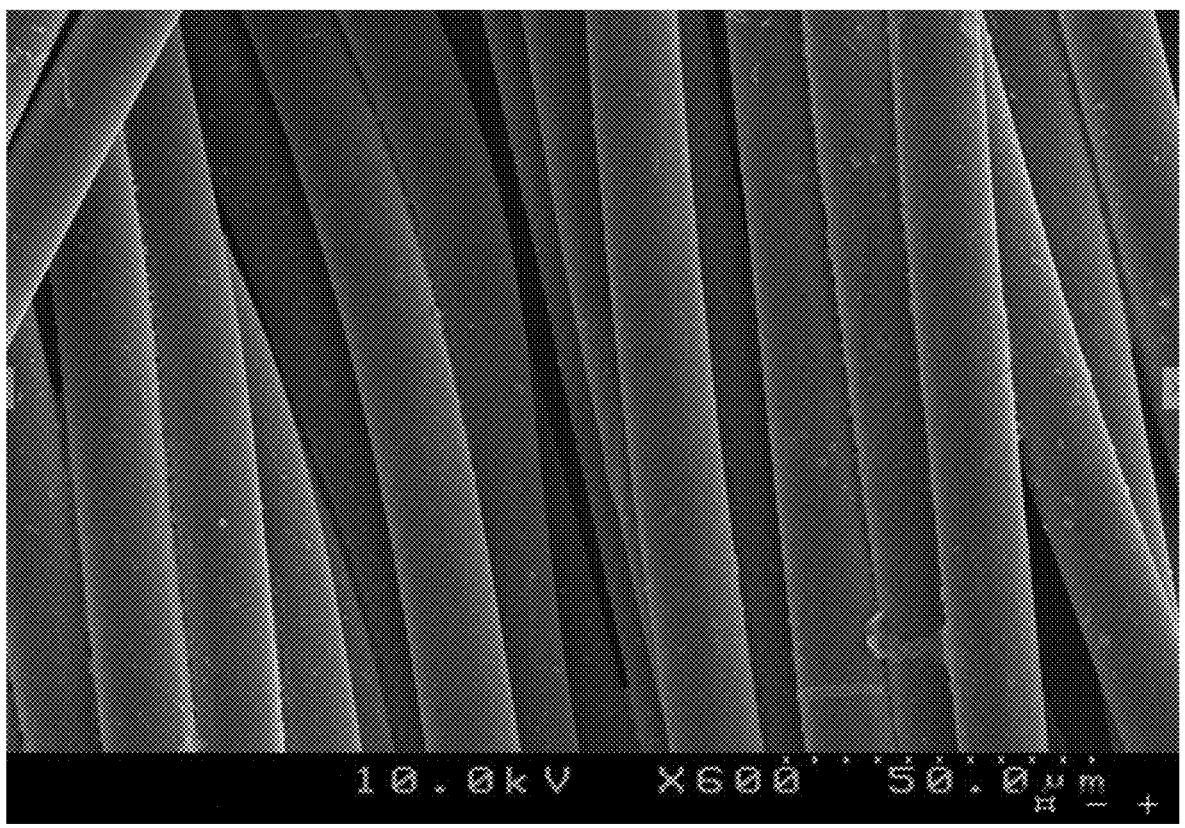
FIGS. 3A and 3B are scanning electron microscopy (SEM) images to verify a degree by which bacteria is adsorbed in an example in which a nonphotocatalyst coating layer is not formed and an example in which a nonphotocatalyst coating layer is formed according to an example embodiment, respectively.
Figure 3B:
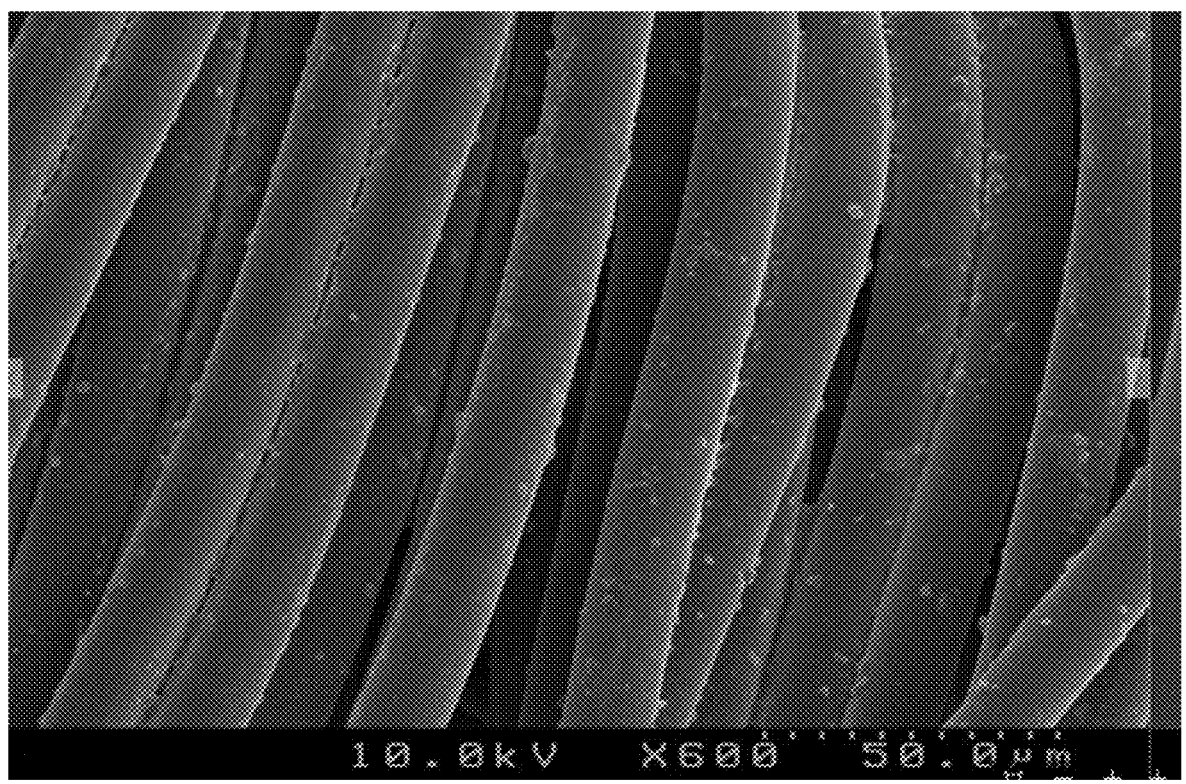

FIGS. 3A and 3B are scanning electron microscopy (SEM) images to verify a degree by which bacteria is adsorbed in an example in which a nonphotocatalyst coating layer is not formed and an example in which a nonphotocatalyst coating layer is formed according to an example embodiment, respectively. For example, when a wound dressing including a nonphotocatalyst coating layer according to an example embodiment is manufactured, a high bacterial adsorption capacity may be implemented.

A thickness of the fabric layer 110 may vary depending on a standard of a product, however, may range, for example, from 0.5 millimeter (mm) to 3 mm.

The bacterial adsorption dressing may further include a support layer 120 and an absorption layer 130. The support layer 120 may include a tencel nonwoven fabric, and may be formed on an opposite side to a side of the fabric layer 110 in contact with the nonphotocatalyst coating layer 200. The absorption layer 130 may include a rayon nonwoven fabric.

The support layer 120 may function to support the bacterial adsorption dressing and secure a durability. The absorption layer 130 may function to absorb oozing. When the absorption layer 130 includes an antibacterial thread, an antibacterial effect may be expected.

The nonphotocatalyst coating layer 200 may be hydrophilic, and may adsorb bacteria by an oxidation reaction.

The nonphotocatalyst coating layer 200 may further include at least one transition metal among Zn, Mn, Fe, Cu, Ni, Co, Cr, V, Zr, Mo, W, Pt and Au.

The nonphotocatalyst coating layer 200 may be hydrophilic and may have a hardness of 6 H to 15 H. Due to a high adhesiveness between the nonphotocatalyst coating layer 200 and a fabric of a fabric layer or a nonwoven fabric layer (for example, an absorption layer or a support layer), a washing durability may be secured. Also, due to an effect of adsorbing bacteria at a level of about 85% or higher, the nonphotocatalyst coating layer 200 may have a secondary infection prevention effect. The remaining bacteria that are not adsorbed in the nonphotocatalyst coating layer 200 may be absorbed by the absorption layer 130.

The titanium dioxide phosphate may have a particle diameter of 6 nm to 15 nm.

The nonphotocatalyst coating layer 200 may have a thickness of 10 micrometers (μm) to 20 μm. For example, when a coating layer is too thick, an adhesive strength to a fabric may decrease and a thickness of a product may increase. When a coating layer is too thin, bacteria may not be effectively adsorbed.

The nonphotocatalyst coating layer 200 may include a microporous surface layer.

A surface layer of the nonphotocatalyst coating layer 200 may have micropores, and accordingly a surface area of the nonphotocatalyst coating layer 200 may increase to enable a contact with bacteria. Thus, the nonphotocatalyst coating layer 200 may have a characteristic of effectively adsorbing bacteria, virus, and the like. Holes in a microporous structure may be formed in the surface layer of the nonphotocatalyst coating layer 200, and bacteria may be attracted by a hydroxyl radical (.OH) reaction around the holes.

The fabric layer 110 may include an inorganic antibacterial material including at least one of zeolite, calcium phosphate, zirconium phosphate and silica gel.

The absorption layer 130 may have a thickness of 500 μm to 2,000 μm and a weight of 60 grams per square meter (g/m$^2$) to 200 g/m$^2$. The support layer 120 may have a thickness of 100 μm to 500 μm and a weight of 20 g/m$^2$ to 60 g/m$^2$. The absorption layer 130 and the support layer 120 may be mechanically bonded to each other.

When the thicknesses of the absorption layer 130 and the support layer 120 are within the above ranges, an appropriate adhesiveness between the fabric layer 110 and the nonphotocatalyst coating layer 200 as well as between the absorption layer 130 and the support layer 120 may be maintained, and an effective bacterial adsorption function and antibacterial function may be performed. A mechanical bonding may indicate that two layers are physically bonded to each other by, for example, a needle instead of by a chemical effect.

The absorption layer 130 may further include an airlaid nonwoven fabric.

Also, the bacterial adsorption dressing may further include a pore nonwoven fabric layer between the fabric layer 110 and the absorption layer 130. The pore nonwoven fabric layer may be formed of a nonwoven fabric including a pore with a size of 2 μm to 10 μm.

In an example, a silicone gel adhesive 300 may be additionally formed on the absorption layer 130. In another example, in a commercialization process, a release paper 400 may be attached onto a top surface, a bottom surface or both of the bacterial adsorption dressing.

Figure 4:
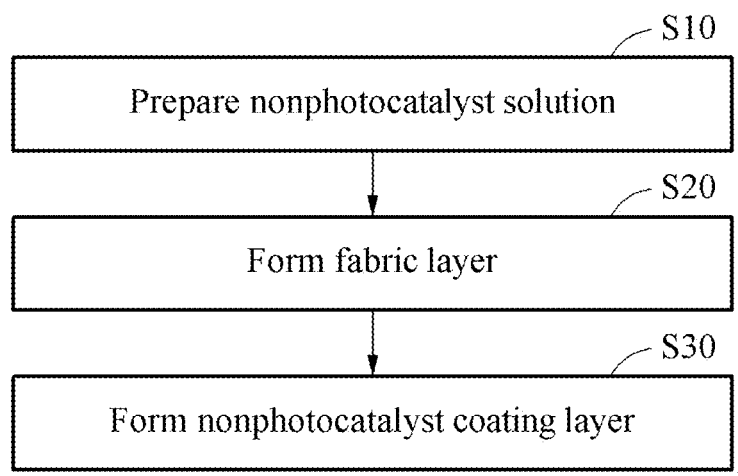
FIG. 4 is a flowchart illustrating a method of manufacturing a bacterial adsorption dressing with a nonphotocatalyst according to an example embodiment.

FIG. 4 is a flowchart illustrating a method of manufacturing a bacterial adsorption dressing with a nonphotocatalyst according to an example embodiment.

Referring to FIG. 4, the method may include operation S10 of preparing a nonphotocatalyst solution, operation S20 of forming a fabric layer including a polyester fabric using a knitting process with a guide bar, and operation S30 of forming a nonphotocatalyst coating layer on the fabric layer using the nonphotocatalyst solution.

In operation S10, a hydrophilic nonphotocatalyst solution may be prepared by mixing a sol-type titanium dioxide with an aqueous transition metal salt solution.

In operation S20, the fabric layer may be formed by a knitting process using a plurality of guide bars.

In operation S30, the nonphotocatalyst coating layer may be formed using one of immersion, spread and spraying.

The method may further include, after operation S30, or between operations S20 and S30, an operation of forming a support layer including a tencel nonwoven fabric on an opposite side to a side of the fabric layer in contact with the nonphotocatalyst coating layer using a spunlace process, an operation of forming an absorption layer including a rayon nonwoven fabric using a needle punching process, and an operation of mechanically bonding the absorption layer and the support layer to each other.

The further operations may be performed after or before each of operations S20 and S30.

In an example, after the fabric layer and the nonphotocatalyst coating layer are formed, the further operations may be performed. In another example, after the fabric layer is formed and the further operations are performed, the nonphotocatalyst coating layer may be formed. When the structure of FIG. 1 is formed by the process, an order of the further operations and operations S20 and S30 is not particularly limited.

The operation of mechanically bonding the absorption layer and the support layer to each other may indicate that two layers are physically bonded to each other by, for example, a needle instead of by a chemical effect.

According to an example embodiment, a fabric layer and a nonwoven fabric layer may be laminated using any one of a Gravure coating method, a comma coating method and a knife coating method.

The spunlace process is a fiber fabrication method of spraying high-pressure water to a fiber and bonding a web. For example, a nonwoven fabric fabricated using the spunlace process may be excellent in flexibility and breathability, and have an effect of enhancing hygienic properties. The needle punching process is a method of fabricating a fiber by physically bonding a web using a special needle. According to an example embodiment, a thickness of a nonwoven fabric layer may vary depending on a number of times of needle punching or a density of needles.

Also, the support layer and the absorption layer may include antibacterial fibers.

According to example embodiments, a bacterial adsorption dressing including a nonphotocatalyst may generate a reactive oxygen through an oxidation reaction by a hydroxyl radical (.OH) by using the nonphotocatalyst even though light is absent. Also, the bacterial adsorption dressing may be excellent in an adhesiveness to a fabric layer even though an organic binder is absent, and may continue to adsorb bacteria due to a high washing durability. Thus, the bacterial adsorption dressing may be easily commercialized.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A bacterial absorption dressing comprising:
   a fabric layer comprising a polyester fiber as a supporter; and
   a coating layer formed on the fabric layer comprising titanium dioxide phosphate, the coating layer being capable of performing a bacterial adsorption function even in a light-free environment,
   wherein the coating layer has a thickness of 10 micrometers ($\mu m$) to 20 $\mu m$,
   wherein the coating layer comprises a microporous surface layer, and wherein the coating layer further comprises at least one transition metal selected from Zn, Mn, Fe, Cu, Ni, Co, Cr, V, Zr, Mo, W, Pt and Au.

2. The bacterial absorption dressing of claim 1, further comprising:
   a support layer comprising a tencel nonwoven fabric and formed on an opposite side to a side of the fabric layer in contact with the coating layer; and
   an absorption layer comprising a rayon nonwoven fabric extending over the support layer such that the support layer is positioned between the absorption layer and fabric layer.

3. The bacterial absorption dressing of claim 1, wherein the coating layer is hydrophilic and absorbs bacteria by an oxidation reaction.

4. The bacterial absorption dressing of claim 1, wherein the titanium dioxide phosphate comprises titanium phosphate particles having a particle diameter of 6 nanometers (nm) to 15 nm.

5. The bacterial absorption dressing of claim 1, wherein the fabric layer comprises an inorganic antibacterial material comprising at least one selected from the group consisting of zeolite, calcium phosphate, zirconium phosphate and silica gel.

6. The bacterial absorption dressing of claim 2, wherein the absorption layer has a thickness of 500 $\mu m$ to 2,000 $\mu m$ and a weight of 60 grams per square meter ($g/m^2$) to 200 $g/m^2$, and the support layer has a thickness of 100 $\mu m$ to 500 $\mu m$ and a weight of 20 $g/m^2$ to 60 $g/m^2$, and the absorption layer and the support layer are mechanically bonded to each other.

7. The bacterial absorption dressing of claim 2, wherein the absorption layer further comprises an airlaid nonwoven fabric.

8. The bacterial absorption dressing of claim 2, further comprising:
   a pore nonwoven fabric layer formed of a nonwoven fabric comprising a pore with a size of 2 $\mu m$ to 10 $\mu m$ and located between the fabric layer and the absorption layer.

9. A method of manufacturing the bacterial absorption dressing of claim 1, the method comprising:
   preparing a solution comprising titanium dioxide phosphate and at least one transition metal salt containing at least one transition metal selected from Zn, Mn, Fe, Cu, Ni, Co, Cr, V, Zr, Mo, W, Pt and Au;
   forming a fabric layer comprising a polyester fabric using a knitting process with a guide bar; and
   forming a coating layer using the solution comprising titanium dioxide phosphate and said at least one transition metal on the fabric layer, wherein the coating layer having a thickness of 10 micrometers ($\mu m$) to 20 $\mu m$.

10. The method of claim 9, further comprising, after the forming of the coating layer, or between the forming of the fabric layer and the forming of the coating layer:
    forming a support layer on an opposite side to a side of the fabric layer in contact with the coating layer using a spunlace process, the support layer comprising a tencel nonwoven fabric;
    forming an absorption layer comprising a rayon nonwoven fabric using a needle punching process such that the support layer is positioned between the absorption layer and fabric layer; and
    mechanically bonding the absorption layer and the support layer to each other.

* * * * *